United States Patent [19]

Allevi et al.

[11] Patent Number: 5,688,925
[45] Date of Patent: Nov. 18, 1997

[54] INTERMEDIATES FOR THE PREPARATION OF DEMETHYLEPIPODOPHYLLOTOXIN

[75] Inventors: Pietro Allevi; Mario Anastasia; Ettore Bigatti; Peter MacDonald, all of Rho, Italy

[73] Assignee: Societa Italiana Cortico-Steroidi S.p.A., Milan, Italy

[21] Appl. No.: 441,210

[22] Filed: May 15, 1995

Related U.S. Application Data

[63] Continuation of Ser. No. 178,340, filed as PCT/EP92/01605, Jul. 15, 1992, abandoned.

[51] Int. Cl.$^6$ .............................. C07H 1/00; C07H 23/00
[52] U.S. Cl. ............................... 536/186; 536/18.1
[58] Field of Search ..................... 536/17.1, 18.1, 536/18.6

[56] References Cited

U.S. PATENT DOCUMENTS

| | | | |
|---|---|---|---|
| 4,564,675 | 1/1986 | Kurabayashi | 536/18.1 |
| 4,757,138 | 7/1988 | Fujii et al. | 536/18.1 |
| 4,871,837 | 10/1989 | Magnusson et al. | 536/4.1 |
| 4,900,814 | 2/1990 | Sterling et al. | 536/18.1 |
| 4,904,768 | 2/1990 | Saulnier et al. | 536/17.1 |
| 4,965,348 | 10/1990 | Saulnier et al. | 536/17.2 |
| 5,036,055 | 7/1991 | Ohnuma et al. | 514/27 |
| 5,041,424 | 8/1991 | Saulnier et al. | 514/27 |
| 5,081,234 | 1/1992 | Ohnuma et al. | 536/17.1 |
| 5,206,350 | 4/1993 | Wang et al. | 536/18.1 |
| 5,386,016 | 1/1995 | Robin et al. | 536/18.1 |

OTHER PUBLICATIONS

Corey et al., *Journal of the Amer. Chem. Soc.*, vol.94 (17) : 6190–6191, (1972).

Lolonde and Chan, *Synthesis*, pp. 817–843, (1985).

*Primary Examiner*—John Kight
*Assistant Examiner*—Howard C. Lee
*Attorney, Agent, or Firm*—Mathews, Collins, Shepherd & Gould, P.A.

[57] ABSTRACT

Demethylepipodophyllotoxin-β-glucosides are prepared by allowing demethylepipodophyllotoxin to react with a 2,3-di-O-ester of a 1-O-trialkylsilyl-4,6-O-alkylidene-β-D-glucose derivative in the presence of a Lewis acid. The 4,6-O-alkylidene group can be alkylidene, arylalkylidene, or heteroarylalkylidene and the 2,3-ester can be lower alkanoyl or haloacetyl. In a typical embodiment, demethylepipodophyllotoxin is allowed to react with 4,6-O-ethylidene-2,3-di-O-acetyl-1-O-trimethylsilyl-β-D-glucose in the presence of boron trifluoride etherate to yield etoposide 2",3"-diacetate.

7 Claims, No Drawings

INTERMEDIATES FOR THE PREPARATION OF DEMETHYLEPIPODOPHYLLOTOXIN

This is a continuation of Ser. No. 08/178,340, filed as PCT/EP92/01605, Jul. 15, 1992, now abandoned.

BACKGROUND OF THE INVENTION

Etoposide and Teniposide are derivatives of Podophyllotoxin which are widely used as anti-cancer agents.

All known processes for their preparation require protection, during the glycosylation step, of the 4'-hydroxy group of 4'-demethylepipodophyllotoxin (hereinafter named DMEP) and subsequent removal of the protecting group. Both protection and deprotection steps inevitably cause losses, particularly when, as in Swiss Patent 514,578 or European Patent 162,701 the protective acylation must be carried out selectively (reaction of only one of the two hydroxy groups present in DHEP).

A further disadvantage of the method described in Swiss Patent 514,578 is that the expensive and toxic reagent benzyl chloroformate must be used for the protection whilst hydrogenation, a difficult and dangerous step to conduct on an industrial scale (especially in a plant designed for the synthesis of anti-cancer compounds) is required for removal of the protecting group.

Various attempts have already been made to reduce losses due to the use of protecting groups.

Thus in European Patents 111,058 and 162,701 protection of DMEP with mono-, di-, and tri-haloacetyl protecting groups is said to give reduced losses during their removal and to lead to products with lower impurity contents.

In order to avoid the necessity to selectively protect the phenolic hydroxy group of DMEP (which also contains a benzyl hydroxy group) European Patent 226,202 describes an indirect method for the preparation of DMEP-4'-acetate by acetylation of DMEP bromide, followed by hydrolysis of the bromo group. No mention is made of the yield in this step. Moreover, the removal of the acetyl protecting group after glycosylation is only achieved by heating under reflux for 48 hours with zinc acetate in methanol and is apparently accompanied by significant amounts of degradation, requiring that the product obtained be purified by gradient column chromatography (again no yields are given).

Etoposide of Formula I:

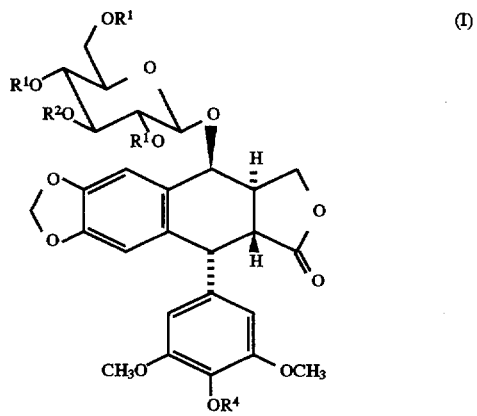

(I)

wherein the groups $R^1$ taken together are ethylidene; $R^2$ is H; $R^4$ is H;
has previously been prepared ( Swiss patent 514,578, European Patents 111,058 and 162,701) by reaction between 2,3-O-diacyl derivatives of 4,6-O-ethylidene-β-D-glucose having the Formula II:

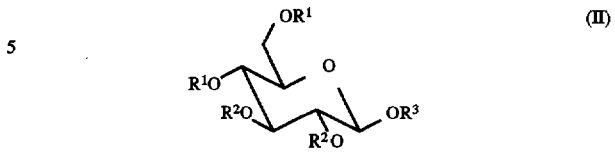

(II)

wherein both $R^1$ groups together are ethylidene, $R^2$ is acetyl, formyl or halo acetyl and $R^3$ is H, and 4'-acylated derivatives of DMEP having the Formula III:

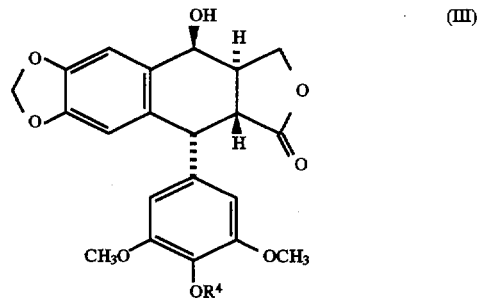

(III)

wherein $R^4$ is acetyl, carbobenzyloxy or haloacetyl to give the corresponding Etoposide triesters of Formula I, where both $R^1$ groups together are ethylidene, $R^2$ is acetyl, formyl or halo acetyl, and $R^4$ is carbobenzyloxy, acetyl or halo acetyl followed by removal of the protecting groups.

However, β-D-glucose derivatives of Formula II, where both $R^1$ are alkylidene and $R^3$ is H are difficult and expensive to prepare and known methods for their preparation require the use of the highly toxic reagent benzyl chloroformate; moreover, an hydrogenation step is required for removal of the carbobenzyloxy protecting group.

Reagents of the Formula II wherein both $R^1$ groups together are thenylidene and $R^3$ is H have not previously been described, probably because of the incompatibility of the thenyl group with a hydrogenation step, since it would poison the hydrogenation catalyst.

In order to avoid the complex multistep process required for the preparation of the 4,6-O-alkylidene-β-D-glucose derivatives of Formula I, wherein $R^3$=H, European Patent 226,202 describes alternative reagents having the Formula II, wherein both $R^1$ groups together are ethylidene, $R^2$ is alkyl or chloroalkyl of 1 to 5 carbon atoms and $R^3$ is trialkyl tin, preferably tributyl tin.

Although these reagents are simpler to prepare, they involve the use of organotin compounds which are notoriously toxic and which may not be completely removed from the final product. Reagents of this type wherein $R^1$ is thenyl are not claimed.

Furthermore, the use of these tin reagents does not obviate the need to use a protecting group for DMEP during glycosylation.

Quite recently, S. Hashimoto et al. (*Tetrahedron Letters*, 32, 1653–54 (1991)) described a further process to form β-glycosidic bonds of Podophyllotoxin and 4'-O-demethylepypodophyllotoxin D-glucosides, which, however, requires the previous DMEP protection before reacting it in a highly complex way and with poor results.

SUMMARY OF THE INVENTION

An improved process is provided for the production of DMEP glycosides, including Etoposide and Teniposide.

Also provided are novel intermediates useful for the synthesis of Etoposide and Teniposide which consist of Etoposide 2",3"-diesters of Formula I, where both R¹=ethylidene, R³=lower alkanoyl or haloacetyl, R⁴=H and Teniposide 2",3"-diesters of Formula I, where both R¹=thenylidene, R²=lower alkanoyl or haloacetyl, R⁴=H.

A further aspect of the invention are novel silylated derivatives of β-D-glucose of Formula II (both R¹=alkylidene, R²=lower alkanoyl or halo acetyl, R³=trialkylsilyl).

A further aspect of the invention is a novel compound of Formula IV:

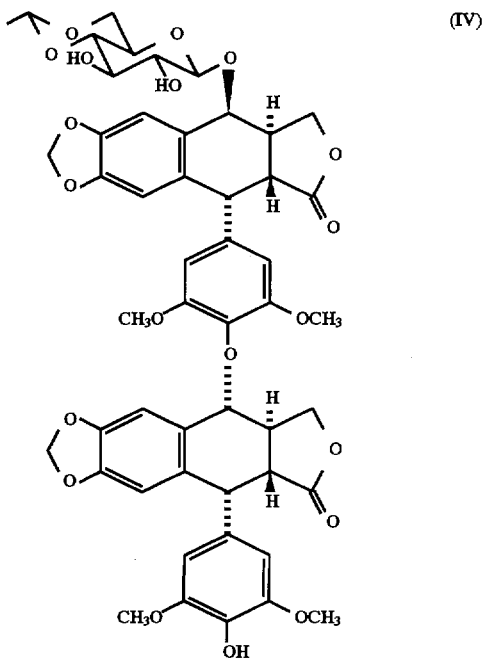
(IV)

its use as an anti-tumour agent, pharmaceutical dosage forms containing it.

DETAILED DESCRIPTION OF THE INVENTION

Surprisingly, in the light of the prior art cited above, it has now been found that glycosylation of DMEP can be carried out without the need to protect the phenolic hydroxy group. The resulting DMEP-glycosides can be obtained in high purity and in almost quantitative yields.

Glycosylation reaction mixtures are normally worked-up by cautious, low-temperature addition of a base (either pyridine or saturated sodium bicarbonate solution). Such treatment, in the presence of free phenolic hydroxy groups leads to extensive formation of "dimeric" products such as that shown in Formula IV.

It has now been found that when the reaction mixture is simply poured into iced water, dimer formation is almost completely suppressed. As a result exceptionally high yields of the desired glycosides are obtained.

These glycosides, which include 2",3"-diesters of Etoposide and Teniposide are novel.

These diester are also valuable intermediates for the production of the corresponding free hydroxy compounds, including Etoposide and Teniposide, which are obtained upon simple hydrolysis.

Preferred diesters which can be prepared by the method of the invention are Etoposide, 2",3"-diformate (I, both R¹=ethylidene, R²=CHO, R⁴=H), Teniposide, 2",3"-diformate (I, both R¹=thenylidene, R²=CHO, R⁴=H), Etoposide, 2",3"-di(dichloroacetate) (I, both R¹=ethylidene R²=dichloroacetate, R⁴=H) and Teniposide 2",3"-di (dichloroacetate) (I, both R¹=thenylidene R²=dichloroacetate, R⁴=H) since these diesters are particularly facile to hydrolyze and give high yields of the corresponding free hydroxy compounds.

According to a further embodiment of the invention there are provided novel β-D-glucose derivatives of Formula II where both R¹=alkylidene, R²=lower alkanoyl or haloacetyl, R³ is trialkylsilyl, preferably trimethylsilyl, which are valuable intermediates for the preparation of β-D-glucosides.

Surprisingly, it has now been found that silylation of either β-D-glucose derivatives of Formula II (R³=H) or the corresponding β-D-glucose isomers leads exclusively to the β-D-glucose silyl derivatives of Formula II (R³=trialkylsilyl).

Since these silyloxy derivatives behave similarly to the corresponding hydroxy compounds during glycosylation reactions catalyzed by Lewis acids such as boron trifluoride, their ease of formation and much lower production costs make them preferable to the free hydroxy compounds for this purpose.

EXAMPLE 1

To a suspension of DMEP (1 kg) and 4,6-O-ethylidene-2,3-O-diformyl-1-O-trimethylsilyl-β-D-glucose (II, both R¹ ethylidene, R²=formyl, R³=trimethylsilyl) (1.8 kg) in dichloromethane (100 l) mantained at about −20° C. under dry nitrogen was added boron trifluoride etherate (1.8 l).

Stirring was continued for about 6 hours after which the reaction mixture was held at about −10° for 30 minutes and then poured quickly into iced-water (100 l) under strong agitation.

The organic phase was separated and again extracted with water (50 l) prior to drying over anhydrous sodium sulphate and evaporation of the solvent.

Addition of methanol (15 l) to the oily residue led to crystallization of Etoposide 2",3"-diformate (I, R¹=ethylidene, R²=formyl, R⁵=H).

A small sample was isolated by filtration, after crystallization from ethyl acetate, had m.p. 262.3°–264.1°.

¹-NMR (500 MHz, CDCl₃, diagnostic signals):

8.048, 7.814 (2H, 2×s, formyl); 4.870 (1H, d, $J_{4,3}$ 3.8 Hz, H-4); 4.792 (1H, d, $J_{1",2"}$ 8.0 Hz, H-1"); 4.336 (1H, dd, $J_{11a,3}$ 10.5 Hz and $J_{11a,11b}$ 8.5 Hz, H-11a); 4.194 (1H, dd, $J_{11b,3}$ 8.0 Hz and $J_{11b,11a}$ 8.5 Hz, H-11b); 3.124 (1H, dd, $J_{2,1}$ 5.3 Hz and $J_{2,3}$ 14.0 Hz, H-2); 2.844 (1H, dddd, $J_{3,4}$ 3.5 Hz, $J_{3,11b}$ 8.0 Hz, $J_{3,11a}$ 10.5 Hz and $J_{3,2}$ 14.0 Hz, H-3).

The bulk of the product was not isolated but hydrolyzed as follows:

To the suspension of Etoposide 2",3"-diformate in methanol was added zinc acetate dihydrate (0.9 kg) and the mixture was heated under reflux for 90 minutes, concentrated under vacuum to about 7 l, diluted with a mixture of water (10 l) and acetic acid (0.5 l) and extracted with dichloromethane (20 l).

The organic extracts were evaporated to dryness and the residue crystallized from ethyl acetate, giving 1.0 kg of Etoposide having a purity of 99%.

An analytical sample obtained by crystallization from dichloromethane/ethanol (recovery about 95%) showed the following characteristics:

1-NMR (500 MHz, CDCl₃ diagnostic signals):

4.890 (1H, d, $J_{4,3}$ 3.5 Hz, H-4); 4.638 (1H, d, $J_{1'',2''}$ 8.0 Hz, H-1"); 3.236 (1H, dd, $J_{2,1}$ 5.5 Hz and $J_{2,3}$ 14.0 Hz, H-2); 2.872 (1H, dddd, $J_{3,4}$ 3.5 Hz and $J_{3,11b}$ 8.0 Hz, $J_{3,11a}$ 10.5 Hz and $J_{3,2}$ 14.0 Hz, H-3).

$[\alpha]_D = -104°$ (CHCl$_3$, c=1).

The starting material was prepared as follows:

To a mixture of 4,6-O-ethylidene-α-glucose (1 kg) in pyridine (4.4 l) at −5° was added formic acid (0.9 l) followed by acetic anhydride (1.75 l).

After one hour conversion into the corresponding 1,2,3-triformate (anomeric mixture) was complete and after addition of water (0.6 l) the reaction mixture was held at about 20° for 24 hours.

After evaporation at low temperature the oily residue, consisting of the 2,3-diformate, was partitioned between dichloromethane and water.

The organic phase was dried over anhydrous sodium sulphate, evaporated to dryness, and crystallized from diisopropyl ether.

NMR analysis showed that the product was a mixture of 4,6-O-ethylidene-2,3-di-O-formyl-β-D-glucose and 4,6-O-ethylidene-2,3-di-O-formyl-α-D-glucose in a ratio of about 29:71.

Yield: 0.4 kg.

The above mixture (0.4 kg) in dichloromethane (4 l) and triethylamine (0.3 l) was treated at below −5° with trimethylchlorosilane (0.26 l).

After stirring for 2 hours at 5° the reaction mixture was extracted twice with water, dried over anhydrous sodium sulphate, and evaporated.

The residue crystallized from diisopropyl ether and after filtration and drying 0.44 kg of 4,6-O-ethylidene-2,3-di-O-formyl-1-O-trimethylsilyl-βD-glucose (III, both $R^1$=ethylidene, $R^2$=trimethylsilyl) were obtained, m.p. 180° C. (dec.).

NMR analysis showed the product to be the pure β-anomer (H-1 at δ4.784, $J_{1,2}$=7.5 Hz).

EXAMPLE 2

Reaction of DMEP with 4,6-O-ethylidene-2,3-di-O-acetyl-1-O-trimethylsilyl-β-D-glucose (III, $R^1$, $R^1$=ethylidene, $R^2$=acetyl, $R^3$=trimethylsilyl) as described in Example 1 gave Etoposide 2",3"-diacetate (I, both $R^1$=ethylidene, $R^2$=acetyl, $R^4$=H). M.p. 238° C.

Hydrolysis using methanol/zinc acetate gave Etoposide identical with that described in Example 1.

The starting material 4,6-O-ethylidene-2,3-di-O-acetyl-1-O-trimethylsilyl-β-D-glucose (III, both $R^1$=ethylidene, $R^2$=acetyl, $R^3$=trimethylsilyl) was obtained in a similar manner to that described in Example 1 for the preparation of the corresponding diformate. Thus acetylation of 4,6-O-ethylidene-α-D-glucose using pyridine/acetic anhydride led to the 1,2,3-triacetate (anomeric mixture, α/β about 1:1), obtained as an oil, which underwent partial hydrolysis on treatment with ammonia in methanol/tetrahydrofuran to give the corresponding 2,3-diacetate as an anomeric mixture. Silylation of the latter with trimethylchlorosilane as described under Example 1 gave 4,6-O-ethylidene-2,3-di-O-acetyl-1-O-trimethylsilyl-β-D-glucose in quantitative yield. M.p. 106° C.

EXAMPLE 3

Reaction of DMEP, as described in Example 1, but using 4,6-O-ethylidene-2,3-O-diformyl-β-D-glucose, prepared as described in Swiss Patent 514,578, there was obtained Etoposide 2",3"-diformate identical to that obtained in Example 1.

EXAMPLE 4

Reaction of DMEP, as described in Example 2, but using 4,6-O-ethylidene-2,3-di-O-acetyl-β-D-glucose, prepared as described in Swiss Patent 514,578, there was obtained Etoposide 2",3"-diacetate identical to that obtained in Example 2.

EXAMPLE 5

When the reaction described in Example 1 was repeated (20 g scale), but the product was isolated by quenching the reaction mixture at lower than −20° C. with pyridine or saturated sodium bicarbonate solution, a major by-product was observed by HPLC analysis.

After hydrolysis of the glycosylation product in the normal way (methanol/zinc acetate), the crude product was chromatographed on reversed-phase silica gel RP-18 eluting with acetone/water mixtures.

Crystallization from acetone/ethyl acetate of the early fractions eluted with 26% v/v acetone gave 7 g of pure Etoposide.

Crystallization from ethyl acetate of the later fractions eluted with 26% v/v acetone afforded 4 g of dimer, having Formula IV.

$^1$-NMR (500 MHz, CDCl$_3$, diagnostic signals):
5.278 (1H, $J_{4''',4'''}$ 9.5 Hz, H-4'''); 4.892 (1H, d, $J_{4,3}$ 3.5 Hz, H-4); 4.606 (1H, d, $J_{1'',2''}$ 8.0 Hz, H-1"); 3.280 (1H, dd, $J_{2,1}$ 5.5 Hz and $J_{2,3}$ 14.0 Hz, H-2); 3.056 (1H, dddd, $J_{3''',11a'''}$ 7.5 Hz, $J_{3''',4'''}$ 9.5 Hz, $J_{3''',11b'''}$ 10.5 Hz and $J_{3''',2'''}$ 14.0 Hz, H-3'''); 2.787 (1H, dddd, $J_{3,4}$ 3.5 Hz, $J_{3,11a}$ 7.5 Hz, $J_{3,11b}$ 10.5 Hz and $J_{3,2\ 14.0}$ Hz, H-3); 2.694 (1H, dd, $J_{2''',1'''}$ 4.5 Hz and $J_{2''',2'''}$ 14.0 Hz, H-2''').

EXAMPLE 6

Comparative Example

An experiment was conducted according to Example 2 of Swiss Patent 514,578 but employing, in place of 4'-carbobenzoxy, DMEP.

HPLC analysis of the crude product indicated the formation of Etoposide 2",3"-diformate together with a large amount of a by-product with a much longer elution time by reversed-phase HPLC analysis.

After hydrolysis according to the method described in the normal way two main peaks were visible by HPLC analysis, one of which corresponded to Etoposide (yield about 25% based upon DMEP) whilst a large second peak corresponded to the "dimer" described in Example 5.

EXAMPLE 7

Under the conditions of Example 1, but employing 2,3,4,6-tetra-O-acetyl-1-O-trimethylsilyl-β-D-glucose (Birkhofer et al., Chem. Ber., 97, 2196–2201 (1964)) there was obtained DMEP-2,3,4,6-O-tetraacetyl-β-D-glucoside, crystals from ethanol, m.p. 215°–218°, $[\alpha]_D$ −60.4° (CHCl$_3$, c=1).

Following the procedures described in U.S. Pat. No. 3,254,844, this compound was converted into Etoposide and Teniposide.

EXAMPLE 8

The reaction of DMEP with 4,6-O-ethylidene-2,3-di-)-dichloroacetyl-1-O-trimethylsilyl-β-D-glucose (III, both $R^1$=ethylidene; $R^2$=dichloroacetyl; $R^3$=trimethylsilyl) was carried out as described in Example 1, but extending reaction time from 6 to 12 hours. Etoposide 2″,3″-di (dichloroacetate) (I, both $R^1$=ethylidene; $R^2$=dichloroacetyl; $R^4$=H) was obtained; m.p. 244° C.

Hydrolysis with methanol/zinc acetate gave Etoposide identical to that obtained in Example 1.

The starting material, 4,6-O-ethylidene-2,3-di-O-dichloroacetyl-1-O-trimethylsilyl-β-D-glucose (III; both $R^1$=ethylidene; $R^2$=dichloroacetyl; $R^3$=trimethylsilyl) was obtained in a similar manner to that described in Example 1 for the preparation of the corresponding diformate. Thus, dichloroacetylation of 4,6-O-ethylidene-α-D-glucose, using pyridine/dichloroacetyl chloride, gave 1,2,3-tri (dichloroacetate) in the form of oil, which was subjected to partial hydrolysis by treating with methanol/methylene chloride, to give the corresponding 2,3-di (dichloroacetate) as an anomeric mixture, $[\alpha]_D$=+32° (c=1; $CHCl_3$). Silylation of the latter with trimethylchlorosilane, as described in Example 1, gave 4,6-O-ethylidene-2,3-di-O-dichloroacetyl-1-O-trimethylsilyl-β-D-glucose in quantitative yield, m.p. 107°–110° C. (hexane).

NMR analysis showed the product was the pure β anomer $[\alpha]_D$=–32° ($CHCl_3$ c=1) (H-1 at δ4.85, $J_{1,2}$=7.5 Hz).

We claim:

1. In the process for the preparation of demethylepipodophyllotoxin-β-glucosides in which a glucose derivative and a demethylepipodophyllotoxin derivative are allowed to react in the presence of a Lewis acid, the improvement which comprises allowing a glucose derivative of the formula:

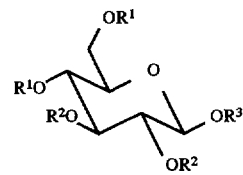

in which the two $R^1$ groups together are alkylidene, arylalkylidene, or heteroarylalkylidene, $R^2$ is lower alkanoyl or haloacetyl, and $R^3$ is trialkylsilyl, to react with demethylepipodophyllotoxin.

2. The process according to claim 1 wherein the two $R^1$ groups together are ethylidene.

3. The process according to claim 2 wherein and each $R^2$ is formyl.

4. The process according to claim 2 wherein and each $R^2$ is dichloroacetyl.

5. The process according to claim 1 wherein the two groups together are thenylidene.

6. The process according to claim 5 wherein and each $R^2$ is formyl.

7. The process according to claim 5 wherein and each $R^2$ is dichloroacetyl.

* * * * *

UNITED STATES PATENT AND TRADEMARK OFFICE
CERTIFICATE OF CORRECTION

PATENT NO. : 5,688,925
DATED : November 18, 1997
INVENTOR(S) : Pietro Allevi, et al It is certified that error appears in the above-identified patent and that said Letters Patent is hereby corrected as shown below:

On the title page, item [73]:

The Assignee's name should read: SICOR SOCIETA' ITALIANA CORTICOSTEROIDI S.p.A.

Signed and Sealed this

Thirteenth Day of October 1998

Attest:

BRUCE LEHMAN

*Attesting Officer*     *Commissioner of Patents and Trademarks*